US005889033A

United States Patent [19]
Kaminski

[11] Patent Number: 5,889,033
[45] Date of Patent: *Mar. 30, 1999

[54] METHOD AND COMPOSITION FOR THE TREATMENT OF APATHY-AMOTIVATION SYNDROME

[75] Inventor: Ram Kaminski, New York, N.Y.

[73] Assignee: Mount Sinai School of Medicine, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 496,608

[22] Filed: Jun. 29, 1995

Related U.S. Application Data

[60] Division of Ser. No. 117,503, Sep. 7, 1993, Pat. No. 5,453,428, which is a continuation-in-part of Ser. No. 954,258, Sep. 30, 1992, Pat. No. 5,352,688, which is a continuation-in-part of Ser. No. 743,254, Aug. 9, 1991, Pat. No. 5,177,081, which is a division of Ser. No. 655,759, Feb. 14, 1991, Pat. No. 5,070,101.

[51] Int. Cl.$^6$ ..................................... A61K 31/41
[52] U.S. Cl. .................. 514/370; 514/471; 514/399; 514/400; 514/365; 514/395; 514/261
[58] Field of Search .................... 514/370, 471, 514/399, 400, 365, 395, 261

[56] References Cited

U.S. PATENT DOCUMENTS

| | | | |
|---|---|---|---|
| 4,171,353 | 10/1979 | Ryan et al. | 514/80 |
| 4,757,060 | 7/1988 | Lukacscko . | |
| 4,806,548 | 2/1989 | Ivanovia et al. | 514/370 |
| 4,876,246 | 10/1989 | Guidon et al. | 514/80 |
| 5,070,101 | 12/1991 | Kaminski . | |
| 5,260,066 | 11/1993 | Wood et al. | 424/447 |
| 5,453,428 | 9/1995 | Kaminski . | |

OTHER PUBLICATIONS

Chem. Abstract 103–52159 y (1985).
Chem. Abstract 110:107925 x (1989).
Chem. Abstract 104:28834 Q (1986).
Kaminski et al., Effect of famotidine on deficit symptoms of schizophrenia, The Lancet, (1990) vol. 335, pp. 1351–1352.
Pickar et al., Neurochemical and Neural Mechanisms . . . , Mod. Probl. Pharmacopsychiatry Basel, (1990) vol. 24 pp. 124–151.
Morrison et al., Positive and Negative Symptoms in Schizophrenia, The Journal of Nervous and Mental Disease, (1990) vol. 178, No. 6 pp. 377–384.
Carpenter et al., Deficit and Nondeficit Forms of Schizophrenia . . . , Am. J. Psychiatry, (1988) vol. 145, No. 5 pp. 578–583.
Wyatt et al., Schizophrenia, just the facts . . . , Schizophrenia Research, (1988) vol. 1 pp. 3–18.
Mesulam, Schizophrenia and Brain, The New England Journal of Medicine, (1990) vol. 322, No. 12 pp. 842–844.
Schwartz et al., Properties and Roles of the Three Subclasses of Histamine . . . , J. Exp. Biol., printed in Great Britain, (1986) vol. 124, pp. 203–224.

Itoh et al., Effects of Nociceptive Stimuli on Brain Histamine Dynamics, Japan, J. Pharmacol. (1989) vol. 49, pp. 449–454.
Gogas et al., Inhibition of Naloxone–Resistant Antinociception . . . , The Journal of Pharmacology and Experimental Therapeutics, (1989) vol. 248, No. 1.
Hough et al., A Role for Histamine and Histamine $H_2$–Receptors . . . , Life Sciences, (1985) vol. 36, pp. 859–866.
Prell, Ann. Rev. Neurosci (1986) vol. 9, pp. 209–254.
Life Sciences, (1985) vol. 36, pp. 859–866.
Heleniak et al., Histamine Methylation in Schizophrenia, Medical Hypotheses, (1989) vol. 30, pp. 167–174.
Heleniak et al., Histamine and Prostaglandins in Schizophrenia, Journal of Orthomolecular Psychiatry, vol. 14, No. 3, pp. 162–177, 1990.
Lucca et al., Biochemical Investigation of Histidinemia . . . Bil. Psychiatry, (1990) vol. 27, pp. 69–75.
Hough, Cellular Localization and Possible Functions for Brain Histamine . . . , Progress in Neurobiology, (1988) vol. 30, pp. 469–505.
White et al., Behavioural effects of histamine and its antagonists: a review . . . , Psychopharmacology, (1988) vol. 95, pp. 1–14.
Emsley et al., Water Excretion and Plasma Vasopressin in Psychotic Disorders, Am. J. Psychiatry (1989) vol. 146, No. 2, pp. 250–253.
Specht et al., Histamine–Elicited Drinking in Weanling and Adult Rate, Physiology & Behavior, (1989) vol. 45, pp. 63–70.
Koczapski et al., Individual Differences in Serum Sodium Level . . . , Am. J. Psychiatry, (1989) vol. 146, No. 12 pp. 1614–1615.
USP DI, (1990), "Histamine $H_2$–Receptor Antagonists (systemic)", pp. 1496–1505.
Gelenberg, "Famotidine for Schizophrenia?—Biological Therapies in Psychiatry" (Newsletter) (1990), vol. 13, No. 11 pp. 41 and 44.
Berkow et al., "The Merck Manual of Diagnosis and Therapy" 14th Edition, published by Merck, Sharp & Dohne Research Laboratorie, (1982), pp. 1359–1362 and 2336–2337.

(List continued on next page.)

*Primary Examiner*—Keith D. MacMillan
*Attorney, Agent, or Firm*—Baker & Botts, L.L.P.

[57] ABSTRACT

In accordance with the present invention, neuropsychiatric symptoms of apathy-amotivation syndrome and particularly those symptoms in: Alzheimer's disease, multiple sclerosis, Huntington's chorea, frontal lobe lesions, and AIDS dementia can be ameliorated by treating a patient with a histamine $H_2$-antagonist that passes the blood-brain barrier. Suitable $H_2$-antagonists include famotidine and ranitidine. The $H_2$-antagonists may be co-administered with other compounds which are known to be useful in the treatment of the above neuropsychiatric conditions, and in one aspect of the invention can be formulated with such other compounds into a therapeutic composition.

2 Claims, No Drawings

OTHER PUBLICATIONS

Bianchine, "Drugs for Parkinson's Disease, Spasticity, and Acute Muscle Spasms", MacMillan Publishing Company, Goodman and Gilman's The Pharmacological Basis of Therapeutics, (1985), 7th Ed., Chap. 21, pp. 473–486.

Engelhardt et al., "Antiparkinsonism Drugs", Medicinal Chemistry, (1985) 3rd Ed. Part II, pp. 1538–1543.

Growden et al., "Distinctive Aspects of Cognitive Dysfunction in Parkinson's Disease", Advances in Neurology, (1990), vol. 53, pp. 3675–3737, Parkinson's Disease: Anatomy, Pathology, and Therapy.

Danilczyk et al., "Psychiatric Complications and Shift of Death Age in Parkinson's Disease", Advances in Neurology, (1990), vol. 53, pp. 405–410 Parkinson's Disease: Anatomy, Pathology and Therapy.

Calne et al., "Parkinson's Disease, Motoneuron Disease and Alzheimer's Disease: Origins and Interrelationship", Advances in Neurology, (1990), vol. 53:355–360.

Agid et al., The Efficacy of Levodopa Treratment Declines in the Course of Parkinson's Disease: Do Nondopaminergic Lesions Play a Role? Advances in Neurology, (1990), vol. 53, pp. 83–100 Parkinson's Disease: Anatomy, Pathology and Therapy.

Cummings, "Depression and Parkinson's Disease: A Review", Am J. Psychiatry, (1992), 149:4, pp. 443–454.

Garbarg et al., "Brain Histidine Decarboxylase Activity in Parkinson's Disease", The Lancet, (1983), pp. 74–75.

Coelho et al., "Decrease in Blood Histamine in Drug–Treated Parkinsonian Patients", Molecular and Chemical Neuropathology, (1991), vol. 14, pp. 77–85.

Poirier et al., "Debrisoquine Metabolism in Parkinsonian Patients Treated with Antihistamine Drugs", The Lancet, (1987), p. 386.

Nakamura et al., "Histochemistry of MPTP Oxidation in the Rat Brain: Sites of Synthesis of the Parkinsonism–Inducing Toxin MPP," Neuroscience Letters, (1986), vol. 65. pp. 321–325.

Cumming et al., "Cerebral Histamine Levels Are Unaffected by MPTP Administration in the Mouse", European Journal of Pharmacology, (1989), vol. 166, pp. 299–301.

Knigge et al., "The Role of Histamine in the Neuroendocrine Regulation of Pituitary Hormone Secretion", Acta Endocrinologica (Copenh), (1991), vol. 124, pp. 609–619.

Cumming et al., "Cerebral Histamine Levels Are Unaffected By MPTP Administration in The Mouse", European Journal of Pharmacology, (1990), vol. 184, pp. 299–301.

Oish et al., "Is Monoamine Turnover in the Brain Regulated by Histamine $H_3$Receptors?", European Journal of Pharmacology, (1990), vol. 184, pp. 135–142.

Cumming et al., "High Affinity Histamine Binding Site Is the $H_3$ Receptor: Characterization and Autoradiographic Localization in Rat Brain", Synapse 8, (1991), pp. 144–151.

Chiavegatto et al., "Effects of Prenatal Diphenydramine Exposure on Dopaminergic Function in Adult Rats", Pharmacology, Biochemistry & Behavior, (1991), vol. 140, pp. 191–193.

Matzen et al., "Brain Regulation of Renin Secretion Involves Central Histaminergic Neurons", Neuroendocrinology, (1990), vol. 52, pp. 175–180.

Sakai et al., "Effects of Thioperamide, A Histamine $H_3$ Receptor Antagonist, on Locomotor Activity and Brain Histamine Content in Mast Cell–Deficient W/W Mice", Life Sciences, (1991), vol. 48, pp. 2397–2404.

Onodera et al., "Pharmacological Characteristics of Catalepsy Induced by Intracerebroventricular Administration of Histamine in Mice: The Importance of Muscarinic Step in Central Cholinergic Neurons", Birkhäuser Verlag, Basel, Agents and Actions, (1991), vol. 33,pp. 143–146.

Knigge, "Histaminergic Regulation of Prolactin Secretion", (1990), vol. 37, No. 2, pp. 109–124.

Eisen et al., "Amyotrophic Lateral Sclerosis, Parkinson's Disease and Alzheimer's Disease: Phylogenetic Disorders of the Human Neocortex Sharing Many Characteristics", Can. J. Neurol. Sci., (1992), vol. 19, pp. 117–120.

Dooneief et al., "An Estimate of the Incidence of Depression in Idiopathic Parkinson's Disease", Arch Neurol, (1992), vol. 49.

Sharpe, "Auditory Attention in Early Parkinson's Disease: An Impairment in Focused Attention", Neuropsychologia, (1992), vol. 30, No. 1, pp. 101–106.

Marin, Am. J. Psychiatry 147:22–30 (1990).

Marin, J. Neuropsychiatry and Clinical Neurosci., 3:243–254 (1991).

Starkstein et al., J. Neuropsychiatry, 4:134–139 (1992).

Bozzola et al., Arch. Neurol., 49:297–300 (1992).

Burns et al., J. Nervous and Mental Dis., 178:20–26, 1991.

Mendez et al., Neurol., 39:349–354 (1989).

Robinson et al., Brain, 107:81–93 (1984).

House et al., Br. J. Psychiatry, 158:83–92 (1991).

Blumer and Benson, in "Psychiatric Aspects of Neurological Disease", Grune and Stratton, pp. 151–166 (1975).

McHugh et al., in "Psychiatric Aspects of Neurological Disease", Grune and Stratton, pp. 267–286 (1975).

Hecaen et al., in "Psychiatric Aspects of Neurological Disease", Grune and Stratton, pp. 137–149 (1975).

Cummings, in "Clinical Neuropsychiatry", Grune and Stratton, pp. 57–67 (19895).

Caine et al., Am. J. Psychiatry 140:6 (1983).

Ho et al., Ann. Internat. Med., 111:400–410 (1989).

Cohen et al., Arch. Neurol., 46:676–680 (1989).

Trimble, Seminars in Neurol., 46:676–680 (1989).

Strub, Arch. Neurol., 46:676–680 (1989).

Wang, Chin. Med. J., 47:199–203 (1991).

Hedreen, Neurosci. Lett., 133:257–261 (1991).

Alvarez, Gehav. Brain Res., 48:127–133 (1992).

Andreasen, ARch. Genl. Psychiatry, 39:784–795 (1982).

Marin et al., Psych. Res., 38:143–162 (1991).

Teri et al., JAGS, 37:109–116 (1989).

Alzheimer, 1977, reprinted in "Neurologic classics in modern translation", Hafner Press, New York, pp. 41–43.

Gilley et al., J. Gerontol., 362–371 (1991).

Halbreich, in "Progress in Psychiatry", Speigel ed., American Psychiatry Press, Inc., Washington, D.C. (1993).

Poeck et al., 1987, in "New Trends in Diagnosis and Management of Stroke", Springer–Verlag, New York.

Petrovich et al., Geriatrics 47:30–38, 1993.

Cooper, in "Head Injury", 3rd Ed., Williams and Wilkins (1993).

Folstein, 1989, "Huntington's Disease: A disorder of families", The Johns Hopkins University Press, Baltimore.

Cacabelos et al., 1989, Meth. Find Exp. Clin. Pharmacol., 11:353–360.

Airaksinen et al., 1991, Neuroscience, 44(2):465–481.

METHOD AND COMPOSITION FOR THE TREATMENT OF APATHY-AMOTIVATION SYNDROME

SPECIFICATION

This application is a division of U.S. application Ser. No. 08/117,503, filed Sep. 7, 1993, now U.S. Pat. No. 5,453,428, which is a continuation-in-part of U.S. patent application Ser. No. 07/954,258, filed Sep. 30, 1992, now U.S. Pat. No. 5,352,688, which is a continuation-in-part of Ser. No. 07/743,254, filed Aug. 9, 1991, now U.S. Pat. No. 5,177,081, which is a divisional of Ser. No. 07/655,759, filed Feb. 14, 1991, now U.S. Pat. No. 5,070,101.

BACKGROUND OF THE INVENTION

This application relates to a method and composition for use in the treatment of apathy-amotivation syndrome (also known as abulia or anergia syndrome) in neuropsychiatric disorders.

The syndrome of apathy is defined as absence of or decrease in motivation (Marin, *Differential Diagnosis and Classification of Apathy*, American Journal of Psychiatry 147: 22–30,, January 1990). Slowness of thinking and diminished ability to shift from one set of thinking to the other. This can occur in a variety of apparently unrelated neuropsychiatric disorders. Some of the most common conditions that result in apathy-amotivation syndrome are: schizophrenia, Parkinson's disease, Alzheimer's disease, multiple sclerosis, Huntington's chorea and frontal lobe lesions. (Marin, *Apathy: A Neuropsychiatric Syndrome*, Journal of Neuropsychiatry and Clinical Neurosciences, 3: 243–254, 1991). In each case apathy-amotivation is just one of a plurality of symptoms associated with the disease. In the past, treatments of other aspects of these conditions such as motor and sensory deficits, dementia, and depression have little or no benefit with respect to apathy-amotivation syndrome.

There is large body of evidence that describe apathy-amotivation syndrome and its manifestation in neuropsychiatric disorders. (Starkstein, et al., *Reliability, Validity, and Clinical Correlates of Apathy in Parkinson's Disease*, Journal of Neuropsychiatry, Volume 4, Number 2, Spring 1992; Bozzola, et al., *Personality Changes in Alzheimer's Disease*, Arch Neurol, Volume 49, March 1992; Burns, et al., *Clinical Assessment of Irritability, Aggression, and Apathy in Huntington and Alzheimer Disease*, The Journal of Nervous and Mental Disease Vol. 178, No. 1; Mendez, et al., *Neurobehavioral changes associated with caudate lesions*, Neurology 39, March 1989; Robinson, et al., *Mood Disorders in Stroke Patients*, Brain (1984); House, et al., *Mood Disorders in the Year after First Stroke*, British Journal of Psychiatry (1991); Benson, et al., *Psychiatric Aspects of Neurological Disease, Personality Changes With Frontal and Temporal Lobe Lesions*, Grune & Stratton, Inc., 1975; Cummings, *Clinical Neuropsychiatry*, Grune & Stratton, Inc., 1985; McHugh, et al., *Psychiatric Aspects of Neurological Disease, Psychiatric Syndromes of Huntington's Chorea: A Clinical and Phenomenologic Study*, Grune & Stratton, 1975; Caine, et al., *Psychiatric Syndromes in Huntington's Disease*, Am J Psychiatry 140:6, June 1983; Ho, et al., *The Acquired Immunodeficiency Syndrome (AIDS) Dementia Complex*, Annals of Internal Medicine, Volume III, Number 5, Sep. 1, 1989; Cohen, et al., *Amantadine Treatment of Fatigue Associated With Multiple Sclerosis*, Arch Neurol Vol. 46, June 1989). The common scientific view is to ascribe apathy-amotivation to deficits in the function of the frontal lobes. (Hecaen, et al., *Psychiatric Aspects of Neurological Disease, Disorders of Mental Functioning Related to Frontal Lobe Pathology*, Grune & Stratton, 1975; Trimble, *Psychopathology of Frontal Lobe Syndromes*, Seminars in Neurology, Volume 10, No. 3, September 1990; Strub, *Frontal Lobe Syndrome in a Patient With Bilateral Globus Pallidus Lesions*, Arch Neurol, Vol. 46, September 1989). In recent years, studies have implicated other brain structures that may be involved in the production of the apathy-amotivation syndrome (e.g., striatum and hippocampal formation) (Wang, *Neurobehavioral Chanaes Following Caudate Infarct: A Case Report with Literature Review*, Chin Med J (Taipei), 1991; Hedreen, et al., *Neuronol loss in layers V and VI of cerebral cortex in Huntington's disease*, Neuroscience Letters, 133 (1991); Alvarez, et al., *The role of histamine in the anterior hypothalamus and its functional interaction with the hippocampal on exploratory behavior in adult male rats*, Behavioural Brain Research, 48: 127–33, 1992) but their specific contribution is yet to be elucidated.

Recently, I have established that apathy-amotivation associated with schizophrenia and Parkinson's disease can be treated using histamine $H_2$-antagonists. It is the object of the present invention to extend this same treatment regimen to patients having apathy-amotivation syndrome associated with other neuropsychiatric disorders.

SUMMARY OF THE INVENTION

In accordance with the present invention, neuropsychiatric symptoms of apathy-amotivation syndrome and particularly those symptoms in: Alzheimer's disease, multiple sclerosis, Huntington's chorea, frontal lobe lesions, and AIDS dementia can be ameliorated by treating a patient with a histamine $H_2$-antagonist that passes the blood-brain barrier. Suitable $H_2$-antagonists include famotidine and ranitidine.

The $H_2$-antagonists may be co-administered with other compounds which are known to be useful in the treatment of the above neuropsychiatric conditions, and in one aspect of the invention can be formulated with such other compounds into a therapeutic composition.

DETAILED DESCRIPTION OF THE INVENTION

The claimed invention relates to the treatment of apathy-amotivation and mental slowing observed in a variety of neuropsychiatric disorders. Some significant examples of these disorders are:

1. Alzheimer's disease;
2. multiple sclerosis;
3. AIDS dementia;
4. frontal lobe syndrome; and
5. Huntington's chorea.

Treatment of other neuropsychiatric disorders exhibiting at least one component of apathy-amotivation or mental slowing are also within the scope of the present invention.

As used herein apathy-amotivation syndrome is typified by slowing of cognitive processes and lack of motivation as manifested by the following:

1. Lack of productivity;
2. Lack of initiative or perseverance;
3. Diminished socialization or recreation;
4. Lack of interest in learning new things;
5. Lack of interest in new experiences;
6. Lack of emotional responsivity to positive or negative events;

7. Unchanging or flat affect; and
8. Absence of excitement or emotional intensity.

All of the above are measurable and quantifiable by well-established psychological testing. (Andreasen, *Negative Symptoms in Schizophrenia*, Archives in General Psychiatry, 39: 784–795, July 1982; Marin, et al., *Reliability and Validity of the Apathy Evaluation Scale*, Psychiatry Research, 38: 143–162, 1991). The syndrome of apathy-amotivation is similar in its manifestation to the negative symptoms of schizophrenia and the bradyphrenia of Parkinson's disease and the pathophysiology may be related although there is no indication that the etiology of these symptoms are the same. Nevertheless, these symptoms respond to the same therapy which I found to be effective for treating schizophrenia (see U.S. Pat. No. 5,070,101, incorporated herein by reference) and Parkinson's disease (see U.S. patent application Ser. No. 07/954,258, incorporated herein by reference). Thus, apathy-amotivation syndrome is treated in accordance with the invention by administering a histamine $H_2$-antagonist that passes the blood-brain barrier to the patient. Suitable histamine $H_2$-antagonists included famotidine, ranitidine, cimetidine, nizatidine, omeprazole, tiotidine and aminofurazan compounds.

The preferred mode of administration is oral administration. Preparations of oral administration can be formulated in various forms (e.g., liquid, tablets, capsules) and may include appropriate excipients, flavorants, colorants, and other carrier materials. Other modes of administration, including intraperitoneal, intravenous and intramuscular administration can be employed, however, particularly if the patient is uncooperative.

In addition to the $H_2$-antagonists and appropriate carrier materials, the pharmaceutical preparation may include one or more agents effective against other symptoms of the above mentioned neuropsychiatric disorders.

In the case of Alzheimer's disease, the dominant feature of the illness is gradual deterioration of memory capacity, (Teri, et al., *Behavioral Disturbance, Cognitive Dysfunction, and Functional Skill*, JAGS Vol. 37, No. 2, February 1989) but it has been known even from the first description of the illness by Alzheimer (Alzheimer, *A unique illness involving the cerebral cortex*, originally published 1907. In Hochberg, C. N., Hochberg, F. H., trans. Neurologic classics in modern translation. New York: Hafner Press: 41–43, 1977) that the patients present a variety of other neuropsychiatric symptoms. Symptoms of apathy, delusions and hallucinations and irritability were found at every level of illness severity in Alzheimer's disease. (Gilley, et al., *Predictors of Behavioral Disturbance in Alzheimer's Disease*, Journal of Gerontology: Psychological Sciences, 1991). Suitable additional pharmaceutical agents may include psychostimulants (e.g., ritalin), Antidepressants (e.g., tricyclics, heterocyclics, MAO inhibitors, serotonin enhancers, and wellbutrin), acetyl-choline precursors (e.g., deanol, choline and lecitine), muscarinic agonists (e.g., oxotremorine), acetylcholinesterase inhibitors (e.g., physostigmine, tacrine, metrifonate, huperzine A and B) and cholinomimetics (e.g., arecoline), hydergine, notropics (e.g., piracetam pentoxyphylline), noradrenergic agents (e.g., clonidine), nerve growth factor (NGF) and phosphatidylserine.

For multiple sclerosis additional neuropsychiatric symptoms are: spacticity, memory impairment and dementia; mood disorders (depression euphoria and mania); and anxiety. Suitable additional pharmaceutical agents include: baclofen; dantrolene; ACTH, Prednisone (oral and intravenous); immunosuppressive agents such as cyclophosphamide, azathioprine; interferon (alpha, beta, and gamma); copolymer I; monoclonal antibodies and cytokines; antipsychotic agents such as haloperidol; antidepressants such as tricyclics, MAO inhibitors, Selective Serotonin Reuptake Inhibitors (SSRI); anxiolytics such as benzodiazepines; lithium; carbamazepine. (Halbreich, U. (ED). *Multiple Sclerosis: A Neuropsychiatric disorder*. In Progress in Psychiatry, Speigel, (series Ed.), 37. American Psychiatric Press, Inc.: Washington, DC 1993).

For Neuropsychiatric complication of HIV infection and AIDS additional symptoms are:

1. headaches
2. retro-orbital pain
3. photophobia
4. depression
5. mania
6. irritability
7. psychosis
8. AIDS dementia complex:
    mental slowing and inattention, apathy,
    reduced concentration,
    forgetfulness,
    motor abnormalities,
    gait abnormalities (ataxia),
    altered personality, and
    dementia Suitable additional pharmaceutical agents include: Dideoxynucleosides; Zidovudine (Retrovir, AZT); didanozine (ddI); zalcitabine (ddC); phosphonoformate (foscarnet); Glycosylation inhibitors e.g. catanospermine; Antiviral e.g. Interferon alpha, acyclovir(Zovirax).

Miscellaneous
    Amphotericin B, 5-Fluorouracil, 5-Flucytosine,
    Cycloserine, Cytosine arabinose, Ethambutol,
    Etoposide, Gancyclovir (DHPG), Interleukin-2,
    Ketoconazol, 1-Asparaginase, Methotrexate,
    Pentamidine, Procarbazine, Rifampin, Sulfonamides,
    Vinblastine, Vincristine Alternative Therapies
    Dinitrochlorobenzene (DNCB), Multivitamins,
    dextran sulfate, naltrexone, disulfiram, AL-721,
    Compound Q (GLQ223), Hypericin, Cysteine
        precursors, Pentoxyfilline (trental)

Psychotropics
    Antipsychotic medication such as haloperidol (Haldol);
        antidepressants such as tricyclics, Selective Serotonin Reuptake Inhibitors (SSRI) such as prozac,
        Lithium, Anxiolytics such as valium, alprazolam
        (Xanax), Amphetamine psychostimulants such as
        Ritalin.

Frontal lobe syndrome can arise from a variety of causes including stroke, head injury, multi infarct dementia, tumors affecting the frontal lobe, and post encephalitis syndrome. Additional symptoms are: mood lability; decrease or loss of judgment and insight; inappropriate or disinhibited behavior; memory deficit; decrease in attention span; inability to shift set of thinking; difficulties in planning and execution of tasks; motor or sensory deficits specific to other brain areas that may be concomitantly impaired. (Benson, et al., *Psychiatric Aspects of Neurological Disease, Personality Changes With Frontal and Temporal Lobe Lesions*, Grune & Stratton, Inc., 1975; Cummings, *Clinical Neuropsychiatry*, Grune & Stratton, Inc., 1985, Trimble, *Psychopathology of frontal lobe syndromes*, seminars in Neurology, 10: 287–294, 1990).

Given the broad range of causes for frontal lobe syndrome, the range of additional treatments is correspondingly broad. Suitable additional pharmaceutical agents in treating stroke are:

1) Platelet Inhibitors
   a) acetylsalicylic acid
   b) dipyridamole (Persantin)
   c) sulfinpyrazone (Anturano)
2) Anticoagulants
   a) Coumarin (Dicumarol)
   b) heparin
3) Thrombolytic enzymes
   a) tissue plasminogen activator (tPA) (Activase)
   b) streptokinase (Streptase)
   c) urokinase (Abbokinase)
4) (Calcium channel blockers)
   a) nimodipine
   b) hifedipine See, e.g.,
Poeck, K., Ringelstein, E. B., and Hacke, W. (eds.), *New Trends in Diagnosis and Management of Stroke*, Springer-Berlag; New York, 1987.

5) Antihypertensive meds
   a) chlorthalidone. See Petrovich, H., Vogt, T. M., Berge, K. G. *Isolated systolic hypertension: lowering the risk of stroke in older patients*. SHEP Cooperative Research Group. Geriatrics, 47(3), p.30–2, 35–8.

For head injury, additional pharmaceutical agents include:
1) Barbiturates
2) Anticonvulsants—Lorazepam, phenytoin
3) Antihypertensives
4) α-blocking agent—phentolamine
   β-adrenergic blockers—propranolol, labetalol.

See Cooper, P. R. (ed.) *Head Injury* (3rd Ed.) Williams & Wilkins: Baltimore, 1993.

For Huntington Disease (HD) additional symptoms are::
1. Involuntary movements (Chorea, motor restlessness, myoclonus, dystonia, and athetosis).
2. Impairment in voluntary movements e.g. clumsiness, bradykinesia.
3. Emotional symptoms: depression, mania, delusions, hallucinations, anxiety irritability.
4. cognitive symptoms: Apathy, slowness of thinking, decrease in attention, decreased ability to shift set, memory loss.

Suitable additional pharmaceutical agents include: antipsychotics such as haloperidol and fluphenazine; antidepressants such as tricyclics, Selective Serotonin Reuptake Inhibitors (SSRI) such as prozac, MAO inhibitors such as nardil; anxiolytics such as benzodiazepines; dopamine depleting agents such as reserpine; mood stabilizers such as lithium and carbamazepine; GABA agonists; beta-blockers such as inderal; glutamate decreasing agents such as baclofen. (Folstein, S. E., *Huntington's Disease: A disorder of families*, The Johns Hopkins University Press: Baltimore, 1989.

Histamine $H_2$-antagonists are administered in amounts; sufficient to ameliorate the symptoms of apathy-amotivation syndrome. It will be appreciated by those skilled in the art that the different histamine $H_2$-antagonists have different effective dosages. For example, if one assumes that famotidine has an effective dosage of 20 to 600 mg/day, preferably 80 to 160 mg/day, then the known equivalent dosage of ranitidine, would be 150 mg–1200 mg/day, preferably 300 mg/day. Unless otherwise specified, the dosages specified herein are "famotidine equivalents," i.e., the dosage for a given histamine $H_2$-antagonist should be adjusted to reflect the difference in effective dosage levels vis-a-vis famotidine.

With the above in mind, $H_2$-antagonists are suitably administered in a famotidine equivalent amount of 20 to 600 mg/day, although the upper limit is imposed by concern over side effects rather than a loss of efficacy. Preferably the $H_2$-antagonist is 'administered in an amount from 80 to 160 mg/day. Pharmaceutical compositions in accordance with the invention are prepared to deliver the effective amount of $H_2$-antagonist in view of the anticipated frequency of treatment.

While not intended to be bound to a particular theory, the efficacy of histamine $H_2$-antagonists in the treatment of apathy-amotivation syndrome is believed to result from a reversal of the effects of elevated histamine levels on the $H_2$ receptors of the brain to increase the level of arousal and motivated behavior. In the case of Alzheimer's disease, it is consistent with the observation that brain histamine levels are altered in Alzheimer's disease. (Cacabelos, et al. *Brain histamine in Alzheimer's disease*, Meth Find Exp Clin Pharmacol, 11: 353–360, 1989). It is also consistent with the fact that the hypothalamus, which is the center for histamine activity is involved in the pathology of Alzheimer's disease. Pathological changes characteristic of Alzheimer's disease were found to be abundant in the hypothalamus. (Airaksinen, et al., *Histamine Neurons in Human Hypothalamus: Anatomy in Normal and Alzheimer Diseased Brains*, Neuroscience Vol. 44, No. 2, pp. 465–481, 1991; Airaksinen, et al., *Neurofibrillary tangles and histamine-containing neurons in Alzheimer hypothalamus*, Agents and Actions, vol. 33, 1/2 (1991)). In addition, other functions regulated by brain histamine, i.e., sleep, eating and body temperature were found to be impaired in Alzheimer's disease. Nevertheless, no association between histamine and the apathy-amotivation symptoms of Alzheimer's disease has been suggested prior to this invention.

I claim:

1. A composition for the treatment of a neuropsychiatric disorder characterized by at least a first and a second set of neuropsychiatric symptoms, the first of which is apathy-amotivation syndrome, comprising:
   (a) a histamine $H_2$-antagonist in an amount effective to ameliorate apathy-amotivation syndrome; and
   (b) a second pharmaceutically active substance in an amount effective in treating the second set of neuropsychiatric symptoms selected from the group consisting of psychostimulants, muscarinic agents, acetylcholinesterase inhibitors and cholinomimetics, hydergine, notropics, noradrenergic agents, and phosphatidyl serine.

2. A composition for the treatment of a neuropsychiatric disorder characterized by at least a first and a second set of neuropsychiatric symptoms, the first of which is apathy-amotivation syndrome, comprising:
   (a) famotidine in an amount effective to ameliorate apathy-amotivation syndrome; and
   (b) a second pharmaceutically active substance in an amount effective in treating the second set of neuropsychiatric symptoms selected from the group consisting of psychostimulants, muscarinic agents, acetylcholinesterase inhibitors and cholinomimetics, hydergine, notropics, noradrenergic agents, and phosphatidyl serine.

* * * * *